US 6,637,263 B2
Oct. 28, 2003

(54) FLOW DIVIDER

(75) Inventors: Hans-Peter Zimmermann, Karlsruhe (DE); Claus Lueth, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/014,252

(22) Filed: Dec. 7, 2001

(65) Prior Publication Data

US 2002/0170351 A1 Nov. 21, 2002

(30) Foreign Application Priority Data

Apr. 4, 2001 (EP) .............................. 01108449

(51) Int. Cl.$^7$ ................................................ G01F 7/00
(52) U.S. Cl. ............................................ 73/195; 73/197
(58) Field of Search ............................. 73/195, 861.2, 73/197, 203, 861.02, 861.03, 861.22, 861.24, 27, 861

(56) References Cited

U.S. PATENT DOCUMENTS

| | | | |
|---|---|---|---|
| 4,794,334 A | * 12/1988 | Kocache et al. | 324/204 |
| 4,800,754 A | 1/1989 | Korpi | 73/202 |
| 5,121,658 A | * 6/1992 | Lew | 73/195 |
| 5,637,790 A | 6/1997 | de Corral | 73/54.06 |

FOREIGN PATENT DOCUMENTS

DE   19914358 A1 * 10/2000 .......... G01N/30/36

OTHER PUBLICATIONS

Koch, A., Examiner. European Search Report, Application No. EP 01 10 8449, dated Sep. 13, 2001.

* cited by examiner

*Primary Examiner*—Harshad Patel

(57) ABSTRACT

The invention relates to a flow divider and a process for dividing a fluid flow into a number of fluid flows, in particular in analytical and/or preparative fluid measurement technology and/or in micro-fluid systems. The flow divider exhibits at least one working sensor, which is assigned to one of the fluid flows and which comprises a control unit for regulating the pressure of one of the fluid flows and/or for regulating one of the fluid flows. The control unit is coupled to the at least one working sensor and to an actuator for changing the fluid flow. At least a number of working sensors corresponding to the number of divided fluid flows is provided, whereby respectively at least one of the working sensors is assigned to one of the fluid flows and whereby the working sensors enable recording of the respective fluid flow. According to the process of the present invention the control unit regulates the fluid flows such that the ratio between at least two of the fluid flows remains substantially constant.

7 Claims, 1 Drawing Sheet

FLOW DIVIDER

BACKGROUND OF THE INVENTION

1. Field of the Invention

The present invention relates to a flow divider for dividing a fluid flow into a number of fluid flows, in particular for analytical or preparative fluid measurement technology and/ or for micro-fluid systems, which has at least one working sensor assigned to one of the fluid flows and which comprises a control unit for regulating the pressure of one of the fluid flows and/or one of the fluid flows, which is coupled to one or each working sensor and an actuator for altering this fluid flow.

2. Discussion of the Background Art

Flow dividers designated as splitters are used in analytical or preparative fluid measurement technology, in particular in association with devices for generating and supplying fluid volume flows in capillaries, preferably in chromatographic separating columns for analytical fluid separating technology. A first application comprises dividing the entire flow generated and supplied by a pump into at least two partial flows, an excess flow in an excess path and a working flow in a working path. In the process the desired working flow in the separating column is adjusted and provided by means of so-called restrictors, that is, by hydraulic resistors arranged in the excess path. To maintain the working flow, that is, the volume flow flowing through the capillaries, substantially constant, depending on the pressure conditions and/or volume conditions in the working path changing as a result of disturbances, for example, DE 199 14 358 A1 discloses a device and a process for providing fluid volume flows in capillaries, which exhibits at least one working sensor and a control unit for regulating the working flow and/or the pressure in the working path, whereby the control unit is coupled to the working sensor and a means for altering the working flow. This device enables the pressure and/or the working flow to be measured and kept constant advantageously in the working path, yet allows this device no corresponding possibilities and measures in the other splitter branch, that is, the excess path in this case.

Another preferred application of such splitters in analytical or preparative fluid measurement technology and/or micro-fluid technology comprises splitting the fluid coming through the separating column or the separating channel into two or more fluid flows, so that these can be supplied to fraction collectors and/or mass spectrometer detectors arranged downstream. Passive splitters are used chiefly for this, that is, individual elements which exhibit a different hydraulic flow resistance. Splitters with back pressure controllers have also become known, whereby the back pressure is kept constant in one of the split branches only. Individually it cannot be avoided that the volume flow changes depending on the physical properties of the fluid and the fluctuations in pressure in each other splitter.

SUMMARY OF THE INVENTION

It is accordingly an aim of the invention to make available a flow divider having a reduced back pressure sensitivity, enabling the splitting ratio to be kept constant independently of the physical properties of the fluid and/or the fluctuations in pressure.

This task is solved according to the present invention by the features of claim 1, in particular in that at least a number of working sensors corresponding to the number of divided fluid flows is provided, whereby respectively at least one of the working sensors is assigned to one of the fluid flows and whereby the working sensors enable recording or measuring of the respective fluid flow assigned to this working sensor.

With the flow divider according to the present invention the volume of the splitter branches can be adjusted according to the splitting ratio such that the fluid front respectively progresses parallel. In this way media-specified breakdowns occur isochronously so that they can be compensated.

The foregoing measures enable the split ratio between each two of the fluid flows to be precisely specified and/or be kept constant. By at least a number of the working sensors assigned to the affected fluid flows corresponding to the number of divided fluid flows being provided, the splitter according to the present invention can be operated independent of media, that is, the split ratio and/or the volume flow can be kept constant in at least one splitter branch independently of the physical properties of the fluid. In contrast to the passive splitters known from the prior art, in which the split ratio is either unknown or detectable only by expensive calibrating, the splitter according to the present invention concerns an active splitter. Via the abovementioned measures the principal drawback of the passive splitters known from the prior art, namely the back pressure sensitivity, can be decreased or completely eliminated. Such active splitters are also distinguished by a greater application flexibility, as they can be employed in all areas where a number of partial flows is to be split off from a single fluid flow.

With the flow divider according to the present invention and realised as an active splitter a fluid flow or influx can be divided into two to n partial flows. The ratio of the individual partial flows can either be firmly preset or adjusted according to the user and application requirements. Typical values for the splitter ratios realisable with such active splitters are 1:1 to 1:10000. It is understood that n−1 partial flows can also be split off using the flow divider according to the present invention.

The number, arrangement and type according to the present invention of the working sensors enable different properties of the fluids flowing through the flow divider, for example their viscosity or thermal capacity, to be compensated advantageously and calculated by means of a computer unit coupled to the control unit. In this way the widest range of measuring principles, such as for example differential pressure measurement or thermal processes, can be utilised advantageously. This is particularly beneficial because for the preferred flow region between approximately 10 nl/min to approximately 1000 ml/min, in particular from 1 nl/min to 100 ml/min, no direct measuring processes independent of the properties of the fluids are known to date and because frequently calibration is not possible, as the fluid mixtures being worked with are unknown.

It is effective here if the working sensors are designed as flow sensors directly measuring the fluid flow, in particular as thermal or thermally pulsed mass flow rate meters or as volumetric flow rate meters. This enables a comparatively simple structure for the flow divider and a comparatively simple computer evaluation of the measurement signals, because in this case the splitter ratio can be determined directly by simple relational development of the measuring values.

In the case where the flow divider is provided with such working sensors whose measurement signals depend on the physical properties of the fluid flowing through the flow divider and whose flow rate or volume flow is to be determined, working sensors are to be provided which are of identical design in this respect.

At least one of the working sensors is assigned advantageously to each of the divided fluid flows. The splitting ratio can be determined directly and/or kept constant particularly easily by this.

If an adjustable actuator for changing the respective fluid flow is assigned to each of the divided fluid flows, the splitting ratio and thus the volume flow can be kept constant in each branch. Sample analysis can be performed parallel in each branch by this, enabling a particularly economical method of operation.

It is effective, if the actuator or each actuator exhibits a continuously changeable hydraulic flow resistance. Electromagnetic regulating valves and/or temperature-controlled actuators can be used, by way of example. Independently of whether variable restrictors adjustable step by step or continuously adjustable are used, they must have an adequate dynamic range, that is, the flow resistance must be adjustable in correspondingly broad limits in order to be able to equalise the possible external fluctuations in back pressure, dependent of the respective applications, by corresponding change of the hydraulic resistance.

According to a preferred field of application the flow divider is effectively arranged such that it enables division into fluid flows in a range of application or working sphere of approximately 10 nl/min to approximately 1000 ml/min, whereby applications to a microrange of approximately 1 nl/min are conceivable, if required.

The present task is solved also by a process for dividing a fluid flow into a number of fluid flows, in particular in analytical or preparative fluid measurement technology and/or in micro-fluid systems, whereby a control unit which is coupled to at least one working sensor, which is assigned to one of the fluid flows, and to an actuator for changing this fluid flow, regulates the pressure of one of the fluid flows and/or regulates one of the fluid flows, characterised in that by means of at least a number of working sensors corresponding to the number of divided fluid flows, of which respectively at least one is assigned to one of the fluid flows, the respective fluid flow is measured and whereby the control unit regulates the fluid flows such that the ratio between at least two of the fluid flows remains substantially constant.

The abovementioned characteristics contribute both individually and in any combination to diminishing the back pressure sensitivity when one fluid flow is divided into a number of fluid flows, and enable the volume flow to be kept constant independent of the physical properties of the fluid assigned thereto and the fluctuations in pressure in this fluid in at least one splitter branch.

BRIEF DESCRIPTION OF THE DRAWINGS

Further features, viewpoints and advantages of the invention will emerge from the following description, wherein two preferred embodiments of the invention are described in greater detail with reference to the figures, in which.

DETAILED DESCRIPTION OF THE INVENTION

Figure 1:
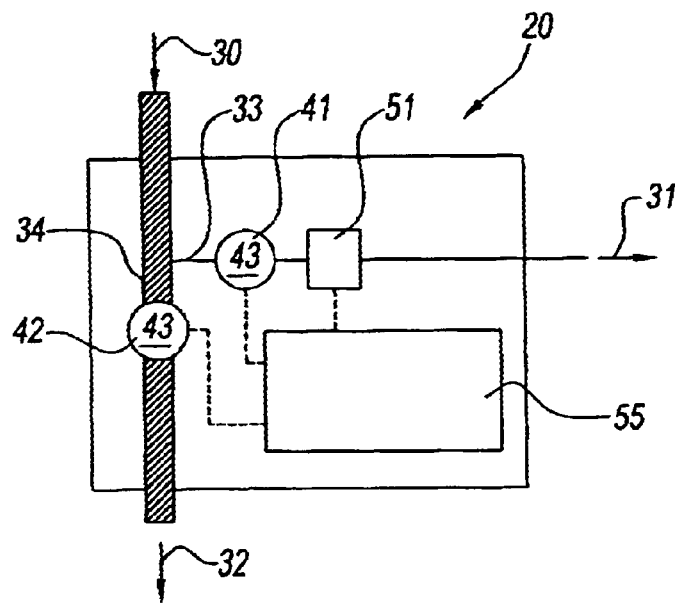
FIG. 1 is a diagrammatic view of a first embodiment of the invention having a flow divider arranged as a 1- to 2-way splitter.

FIG. 1 illustrates flow divider 20 according to a first embodiment of the invention, which is arranged here as a 1- to 2-way splitter. This means that flow divider 20 divides inflowing fluid flow 30 into 2 partial flows, designated here as fluid flow 31 and fluid flow 32. The divided fluid flows 31 and 32 are accordingly assigned to a first splitter branch 33 and a second splitter branch 34. Disposed in first splitter branch 33 is a working sensor 41 designed as a flow sensor and an actuator 51 is arranged downstream, whereas only one working sensor is arranged as flow sensor 42 in second splitter branch 34. Working sensors 41 and 42 as well as actuator 51 are coupled by means of electrical wires for example to a control unit 55, as illustrated in FIG. 1 by the dashed lines. In the embodiment illustrated control unit 55 comprises a computer unit. The computer unit serves to calculate the splitter ratio, that is, the ratio of the volume rates of fluid flow 31 and of fluid flow 30 from the measurement signals detected by working sensors 41 and 42. It is contemplated that working sensors 41 and 42 are thermal or thermally pulsed mass flow rate meters 43. The result is converted in control unit 55 into a corrective signal for an actuator 51. Depending on the self-adjusting back pressure downstream of actuator 51 in first splitter branch 33 fluid flow 31 is changed and consequently fluid flow 32 also, whereby the respective changes are detected by working sensors 41 and 42 and forwarded to control unit 55. This control unit 55 regulates fluid flows 31 and 32 using an appropriate algorithm such that the ratio between both these fluid flows remains substantially constant. In the embodiment of the 1- to 2-way splitters this means that by necessity fluid flow 31 is regulated to an essentially constant value, as inflowing fluid flow 30 can be assumed to be constant. An example of a typical splitting ratio between fluid flows 31 and 32 is 1/1000.

Each of the four splitter branches 75, 76, 77, 78 comprises a working sensor 81, 82, 83, 84 designed as flow sensor to which an actuator 91, 92, 93, 94 is respectively connected downstream. Likewise for flow divider 20 of the first embodiment according to FIG. 1, with the second embodiment of flow divider 60 according to FIG. 2 working sensors 81, 82, 83, 84 are realised identically with respect to the dependence of their measurement signals on the physical properties of the fluid to be measured. This means that when a change is made to the physical properties of the fluid in respective splitter branches 33, 34; 75, 76, 77, 78 the respective relative changes of the measurement signals of individual flow sensors 41, 42; 81, 82, 83, 84 proceed identically in strength and direction. This enables the volume flow to be determined and/or kept constant in individual splitter branches 33, 34; 75, 76, 77, 78 or the respective splitting ratios to be determined and/or kept constant independently of the respective physical properties of the fluid and/or the fluctuations in pressure in respective splitter branches 33, 34; 75, 76, 77, 78 by ratio development or calculation in the computer unit of control unit 55. It is contemplated that working sensors 81, 82, 83, 84 are volumetric flow rate meters 85.

Each of the four splitter branches 75, 76, 77, 78 comprises a working sensor 81, 82, 83, 84 designed as flow sensor to which an actuator 91, 92, 93, 94 is respectively connected downstream. Likewise for flow divider 20 of the first embodiment according to FIG. 1, with the second embodiment of flow divider 60 according to FIG. 2 working sensors 81, 82, 83, 84 are realised identically with respect to the dependence of their measurement signals on the physical properties of the fluid to be measured. This means that when a change is made to the physical properties of the fluid in respective splitter branches 33, 34; 75, 76, 77, 78 the respective relative changes of the measurement signals of individual flow sensors 41, 42; 81, 82, 83, 84 proceed identically in strength and direction. This enables the volume flow to be determined and/or kept constant in individual splitter branches 33, 34; 75, 76, 77, 78 or the respective splitting ratios to be determined and/or kept constant independently of the respective physical properties of the fluid and/or the fluctuations in pressure in respective splitter branches 33, 34; 75, 76, 77, 78 by ratio development or calculation in the computer unit of control unit 55.

Both flow divider 20 and flow divider 60 are realised as active splitters. This means that said splitters 20, 60 are able to eliminate the main disadvantage of passive splitters common in the prior art, namely a sensitivity to back pressure in the respective splitter branches. The flow dividers are preferably designed as a separately manageable unit.

Figure 2:
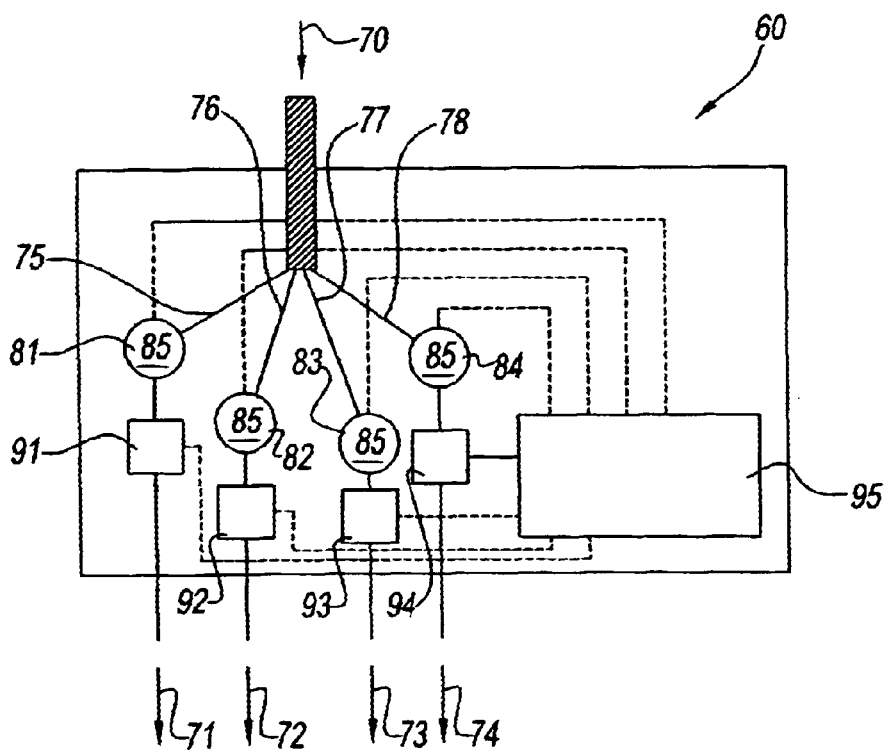
FIG. 2 is a diagrammatic view of a second embodiment of the invention having a flow divider arranged as a 1- to 4-way splitter.

Likewise for actuator 51 of flow divider 20 according to the first embodiment with actuators 91, 92, 93, 94 of flow divider 60 according to the second embodiment, it is a case of variable restrictors, that is, adjustable actuators which are variable with respect to their hydraulic flow resistance. The hydraulic resistance of the respective actuators can be changed preferably continuously, thus enabling constant regulation of the volume flow or flows. Both working sensors 81, 82, 83, 84 and actuators 91, 92, 93, 94 are coupled to control unit 95 by electrical wires, by way of example, as illustrated in FIG. 2 by way of dashed lines. It is understood, however, that the coupling may be in any form, in particular in the form of electromagnetic waves or similar.

In accordance with a preferred application of flow dividers 20, 60 they are used in analytical or preparative fluid separation technology either for dividing a whole flow conveyed by a supply device, in particular a pump, into an excess flow in an excess path and a working flow in a working path, wherein a separating mechanism, in particular a separating column, is arranged, or flow dividers 20, 60 are arranged downstream in the working path after the separating mechanism, in particular after the separating column. The working flow is divided up by flow dividers 20, 60 into at least two or more fluid flows 31, 32 or 71, 72, 73, 74, therefore into at least two or more splitter branches 33, 34 or 75, 76, 77, 78. After they pass working sensors 41, 42; 81, 82, 83, 84 and actuators 51; 91, 92, 93, 94 fluid flows 31, 32; 71, 72, 73, 74 divided into corresponding splitter branches 33, 34; 75, 76, 77, 78 are directed to appropriate detectors which can also be designed as mass-spectrometer detectors. Fraction collectors, in which the fluids or fluid mixtures to be collected can be collected according to content, can be attached to the detectors in an application in the area of preparative fluid separation technology.

LIST OF REFERENCE NUMBERS

| | |
|---|---|
| 20 | Flow divider |
| 30 | Fluid flow |
| 31 | Fluid flow |
| 32 | Fluid flow |
| 33 | First splitter branch |
| 34 | Second splitter branch |
| 41 | Working sensor |
| 42 | Working sensor |
| 51 | Actuator |
| 55 | Control unit |
| 60 | Flow divider |
| 70 | Fluid flow |
| 71 | Fluid flow |
| 72 | Fluid flow |
| 73 | Fluid flow |
| 74 | Fluid flow |
| 75 | First splitter branch |
| 76 | Second splitter branch |
| 77 | Third splitter branch |
| 78 | Forth splitter branch |
| 81 | Working sensor |
| 82 | Working sensor |
| 83 | Working sensor |
| 84 | Working sensor |
| 91 | Actuator |
| 92 | Actuator |
| 93 | Actuator |
| 94 | Actuator |
| 95 | Control unit |

What is claimed is:

1. A flow divider for an incoming flow of fluid comprising:
   means for dividing the incoming flow of fluid into a first partial fluid flow and a second partial fluid flow;
   a first working sensor for generating a first signal indicative of said first partial fluid flow;
   a second working sensor for generating a second signal indicative of said second partial fluid flow;
   a first actuator for changing said first partial fluid flow;
   a second actuator for changing said second partial fluid flow; and
   a control unit in electrical communication with said first and second actuators and said first and second working sensors, said control unit calculating a ratio of said first partial fluid flow to said second partial fluid flow from said first and second signals, said control unit providing a corrective signal to said first actuator and/or said second actuator to maintain said ratio substantially constant.

2. The flow divider as in claim 1, wherein said first and second working sensors are fluid flow sensors directly measuring a flow rate of said first and second partial fluid flows, respectively.

3. The flow divider as in claim 2, wherein said first and second working sensors are selected from the group consisting of mass flow rate meters and volumetric flow rate meters.

4. The flow divider as in claim 1, wherein said first and second actuators are downstream of said first and second working sensors, respectively.

5. The flow divider as in claim 1, wherein said first and second partial fluid flows are unrestricted upstream of said first and second actuators.

6. The flow divider as in claim 1, wherein said ratio of said first partial fluid flow to said second partial fluid flow is 1 to 1000.

7. The flow divider as in claim 1, wherein said dividing means divides the incoming flow of fluid into more than two partial fluid flows, each of said more than two partial fluid flows comprises a working sensor for generating a signal indicative of its partial fluid flow and an actuator for changing its partial fluid flow.

\* \* \* \* \*